(12) United States Patent
Meier

(10) Patent No.: US 9,827,065 B2
(45) Date of Patent: Nov. 28, 2017

(54) TOMOGRAPHY APPARATUS WITH INTEGRATED LIGHTING

(71) Applicant: SIEMENS AKTIENGESELLSCHAFT, Munich (DE)

(72) Inventor: Norman Meier, Pottiga (DE)

(73) Assignee: Siemens Aktiengesellschaft, Munich (DE)

( * ) Notice: Subject to any disclaimer, the term of this patent is extended or adjusted under 35 U.S.C. 154(b) by 274 days.

(21) Appl. No.: 14/442,568

(22) PCT Filed: Oct. 24, 2013

(86) PCT No.: PCT/EP2013/072254
§ 371 (c)(1),
(2) Date: May 13, 2015

(87) PCT Pub. No.: WO2014/075885
PCT Pub. Date: May 22, 2014

(65) Prior Publication Data
US 2016/0287347 A1  Oct. 6, 2016

(30) Foreign Application Priority Data
Nov. 13, 2012 (DE) .......................... 10 2012 220 599

(51) Int. Cl.
| | |
|---|---|
| *A61B 90/30* | (2016.01) |
| *A61B 6/08* | (2006.01) |
| *A61B 6/00* | (2006.01) |
| *A61B 5/055* | (2006.01) |
| *A61B 6/03* | (2006.01) |
| *G01R 33/30* | (2006.01) |

(Continued)

(52) U.S. Cl.
CPC .............. *A61B 90/30* (2016.02); *A61B 5/055* (2013.01); *A61B 6/032* (2013.01); *A61B 6/08* (2013.01); *A61B 6/4007* (2013.01); *A61B 6/4435* (2013.01); *A61B 6/4447* (2013.01); *A61B 6/486* (2013.01); *G01R 33/30* (2013.01); *G01R 33/34* (2013.01); *G01R 33/48* (2013.01); *A61B 2090/309* (2016.02)

(58) Field of Classification Search
CPC ........... A61B 6/588; A61B 6/589; A61B 6/04; A61B 6/587
USPC .................................................. 378/205, 206
See application file for complete search history.

(56) References Cited

U.S. PATENT DOCUMENTS

| | | | |
|---|---|---|---|
| 4,385,397 | A | 5/1983 | Verro |
| 5,038,260 | A | 8/1991 | Scheibengraber |
| 5,533,082 | A | 7/1996 | Gronemeyer et al. |

(Continued)

FOREIGN PATENT DOCUMENTS

| | | |
|---|---|---|
| CN | 102090899 A | 6/2011 |
| DE | 102010032754 A1 | 2/2013 |

(Continued)

*Primary Examiner* — Don Wong
(74) *Attorney, Agent, or Firm* — Schiff Hardin LLP

(57) ABSTRACT

A tomography apparatus has a gantry with an exterior surface, and a tunnel-shaped opening proceeding through the gantry that defines an examination region, from which tomographic data are acquired from a patient in the opening. An illuminant is integrated into the gantry. The illuminant has a light exit window with a smooth transition to the exterior surface of the gantry.

11 Claims, 4 Drawing Sheets

(51) Int. Cl.
*G01R 33/34* (2006.01)
*G01R 33/48* (2006.01)

(56) References Cited

U.S. PATENT DOCUMENTS

| | | | | |
|---|---|---|---|---|
| 6,801,594 | B1* | 10/2004 | Ali | A61B 6/032 |
| | | | | 378/114 |
| 2008/0181359 | A1* | 7/2008 | Stayman | A61B 6/032 |
| | | | | 378/20 |
| 2009/0028292 | A1* | 1/2009 | Popescu | A61B 6/032 |
| | | | | 378/19 |
| 2010/0177867 | A1 | 7/2010 | Kozelj et al. | |
| 2011/0142196 | A1 | 6/2011 | Shinno | |

FOREIGN PATENT DOCUMENTS

| | | |
|---|---|---|
| DE | 102012214169 A1 | 2/2014 |
| DE | 102012214170 A1 | 2/2014 |
| DE | 102012215130 A1 | 2/2014 |
| GB | 2112260 A | 7/1983 |
| JP | 2004089621 A | 3/2004 |
| JP | 2012034973 A | 2/2012 |

\* cited by examiner

TOMOGRAPHY APPARATUS WITH INTEGRATED LIGHTING

BACKGROUND OF THE INVENTION

Field of the Invention

The invention relates to a tomography device with integrated lighting.

Description of the Prior Art

Tomography devices are designed to record tomographic images. For example, a tomography device is a magnetic resonance tomography system or a computed tomography system. Such tomography devices have what is known as a gantry, which is a unit with an opening which is designed to receive a patient or another object. Tomography devices can also be used to assist with an invasive treatment such as a biopsy. In this case it is often necessary to record images using a tomography device during the invasive treatment of a patient. Lighting is normally necessary for the invasive treatment, for instance for manual guidance of a biopsy needle by a physician. However, commercially available surgical lights cannot be optimally positioned, since their position is restricted by the tomography device. Furthermore, such surgical lights restrict the scope of movement or even the view of the person carrying out the treatment, so that good illumination of the examination region and an unrestricted view of the examination region with sufficient scope of movement are mutually exclusive.

From DE 10 2010 032 754 A1 a radiography system is known that has an adjustable bracket in the form of a gantry. An X-ray source and an X-ray detector are arranged on the radiography system. At least one illuminant is arranged on the gantry, and is designed to emit light and/or to modify emitted light when a function of the radiography system is triggered. In this case the illuminant is arranged on the interior or an edge of the gantry.

SUMMARY OF THE INVENTION

An object of the invention is to provide lighting for a tomography device, so that the conditions of treatment of an examination region are improved near-instantaneously or simultaneously to a tomographic image recording of the examination region.

In a tomography device having a gantry and an illuminant designed to illuminate an examination region protruding into the opening of the gantry, in accordance with the invention the illuminant is integrated into the gantry such that the surface of the gantry has a smooth transition to the light exit window of the illuminant. Due to the inventive integrated illuminant the conditions for treating the examination region with a simultaneous tomographic recording are improved, so that the person carrying out the treatment is guaranteed greater scope of movement combined with simultaneous illumination of the examination region. Since there is a smooth transition from the surface of the gantry to the light exit window of the illuminant, the illuminant does not protrude, thus reducing the risk of a collision between a person carrying out treatment and/or a medical instrument with the illuminant. Furthermore, it is easier to clean the surface of the gantry and of the light exit window because of the non-protruding construction of the illuminant and the abutting edges which are thereby avoided.

In another embodiment of the invention, the illuminant has multiple lighting elements that can be controlled separately from one another, so that there is greater flexibility for example when regulating the direction and brightness of the lighting.

In another embodiment of the invention, the illuminant is integrated at least partially into the tunnel-shaped opening of the gantry, so that the examination region protruding into the opening is illuminated as directly as possible.

In another embodiment of the invention, the gantry has a funnel-shaped taper leading to the opening, wherein at least one part of the illuminant is integrated into the funnel-shaped taper, so that even regions of the patient which do not protrude into the opening can be well illuminated.

In another embodiment of the invention, the direction of propagation of the light emitted by the illuminant can be adjusted, so that the lighting can be adapted to different treatment conditions and patient geometries.

In another embodiment of the invention, the shadow cast by the illuminant is reduced, in that the illuminant is designed for the simultaneous illumination of the examination region from different directions. By illuminating the examination region from different directions, the respective shadows cast as a result of an incidence of light from a respective other direction are illuminated. Because of the reduction in the shadows cast the treatment of the examination region is facilitated, in particular in invasive interventions.

In another embodiment of the invention, the illuminant extends radially along the opening of the gantry and/or radially along the funnel-shaped taper, so that the examination region is illuminated radially from different directions and hence the shadows cast are reduced.

In another embodiment of the invention, the illuminant extends axially along the opening of the gantry, so that the examination region is illuminated axially from different directions and hence the shadows cast are reduced.

In another embodiment of the invention, the light of the illuminant can be directed onto a localized region, so that the person carrying out the treatment can concentrate particularly well on the treatment of the localized region.

In another embodiment of the invention, the illuminant is an LED, so that the illuminant is designed to be particularly durable and energy-saving. An LED furthermore offers the advantage that it develops less heat, which is particularly important in the case of the inventive lighting as a result of the proximity of illumination source and patient.

In another embodiment of the invention, the illuminant is a halogen lamp, so that the illuminant can provide a particularly high luminous intensity.

In another embodiment of the invention, the tomography device is a CT device, so that it is possible simultaneously to illuminate the examination region and to record a CT image.

In another embodiment of the invention, the tomography device is an MRT device, so that it is possible simultaneously to illuminate the examination region and to record an MRT image.

DESCRIPTION OF THE PREFERRED EMBODIMENTS

Figure 1:
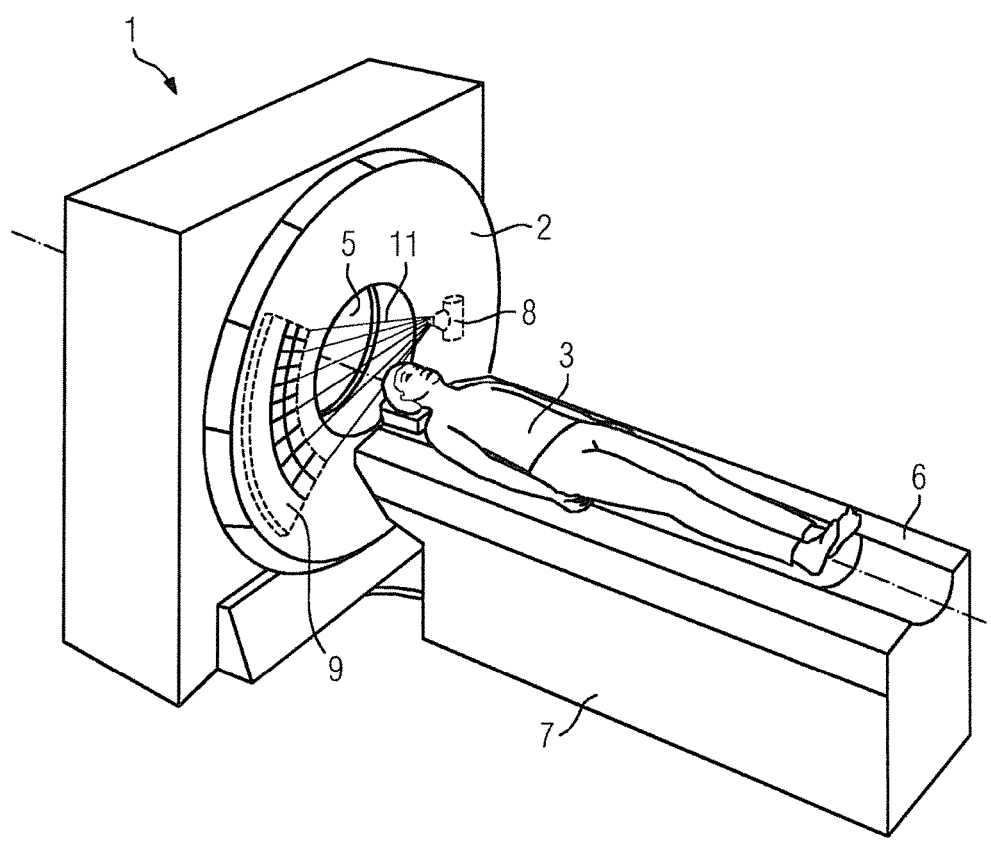
FIG. 1 shows a tomography device in the form of a computed tomography system.

FIG. 1 shows a tomography device in the form of a computed tomography system 1, which has a recording unit comprising an X-ray emitter 8 and an X-ray detector 9. The recording unit is designed to record X-ray projections, which can be reconstructed to form tomographic, three-dimensional images. In this sense the recording unit is designed to record tomographic, three-dimensional images. The recording unit rotates about a longitudinal axis during a recording, and the X-ray emitter 8 emits X-ray radiation 11 during the recording. The computed tomography system 1 can also have more than just one X-ray emitter 8 and more than just one X-ray detector 9 to enable recordings to be taken in the so-called dual-energy procedure. In the example shown here the X-ray emitter 8 is an X-ray tube. In the example shown here the X-ray detector 9 is a line detector with a number of lines. The X-ray detector 9 is normally a scintillator counter. However, the X-ray detector 9 can also be designed as a directly converting detector which converts the highly energized X-ray photons into an electrical signal current by means of a semiconductor material directly by internal photoexcitation using the photovoltaic principle.

The tomography device can, for example, also be an MRT device. In an MRT device the recording unit is designed in the form of at least one RF coil. An individual RF coil can in this case be designed both as a radiation emitter and as a radiation detector. The RF coil can in particular be a local coil, e.g. a head or thoracic coil.

A tomography device 1 has a gantry 2, which is a unit with an opening 5 which is designed to receive a patient 3 or another object. In the case of a computed tomography system 1 the gantry 2 includes the rotatable recording unit. The gantry 2 has a lining, behind which the electronic and mechanical components, coolant, etc. are located. This lining forms a tunnel-shaped opening 5. The tunnel-shaped part of the opening 5 is characterized in that the lining forms a tube with a consistent diameter along the axial direction. Furthermore, in one embodiment of the inventive tomography device, the lined gantry 2 has a funnel-shaped taper 10, which opens into the tunnel-shaped opening 5. A funnel-shaped taper 10 of this type is explained in greater detail in the following figures.

A tomography device is designed to record spatially three-dimensional images of an examination region of a patient 3. The examination region is for example an organ, i.e. the heart, liver or lungs of the patient, as well as the tissue immediately abutting it. However, the examination region can also be defined more broadly, and for instance can comprise the thorax or the abdomen. During the recording of an image the patient 3 lies on a patient table 6 which is connected to a table base 7, such that it supports the patient table 6 with the patient 3. The patient table 6 is designed to move the patient 3 along a recording direction through the opening 5 of the gantry 2.

Tomography devices are increasingly used for imaging of an examination region of a patient 3 in immediate temporal proximity to or during an invasive treatment. Examples of such treatments are the removal of tissue samples, imaging during an emergency examination, or fluoroscopy, for instance in connection with a heart operation. CT fluoroscopy is the continuous recording and reconstruction of tomographic X-ray images. This enables continuously (often several times a second) reconstructed X-ray images of the mapped region to be displayed. For example, fluoroscopy is used—often with the help of a contrast agent—to carry out minimally invasive operations in the cardiovascular system. In such treatments the person carrying out the treatment, for instance a physician, often has to have direct access to the examination region, or it must at least be possible to position medical devices such as tubes, catheters, syringes and/or brackets for such medical devices in immediate proximity to the examination region.

Hence it is important to improve the conditions for treating an examination region near-instantaneously or simultaneously to a tomographic image recording of the examination region. In particular this includes providing lighting for the examination region, so that the person carrying out the treatment can perform necessary interventions precisely. Furthermore, the lighting must not, as to date has often been the case, restrict the scope of movement of the person carrying out the treatment or obstruct the direct view of the examination region by the illuminant itself.

Figure 2:
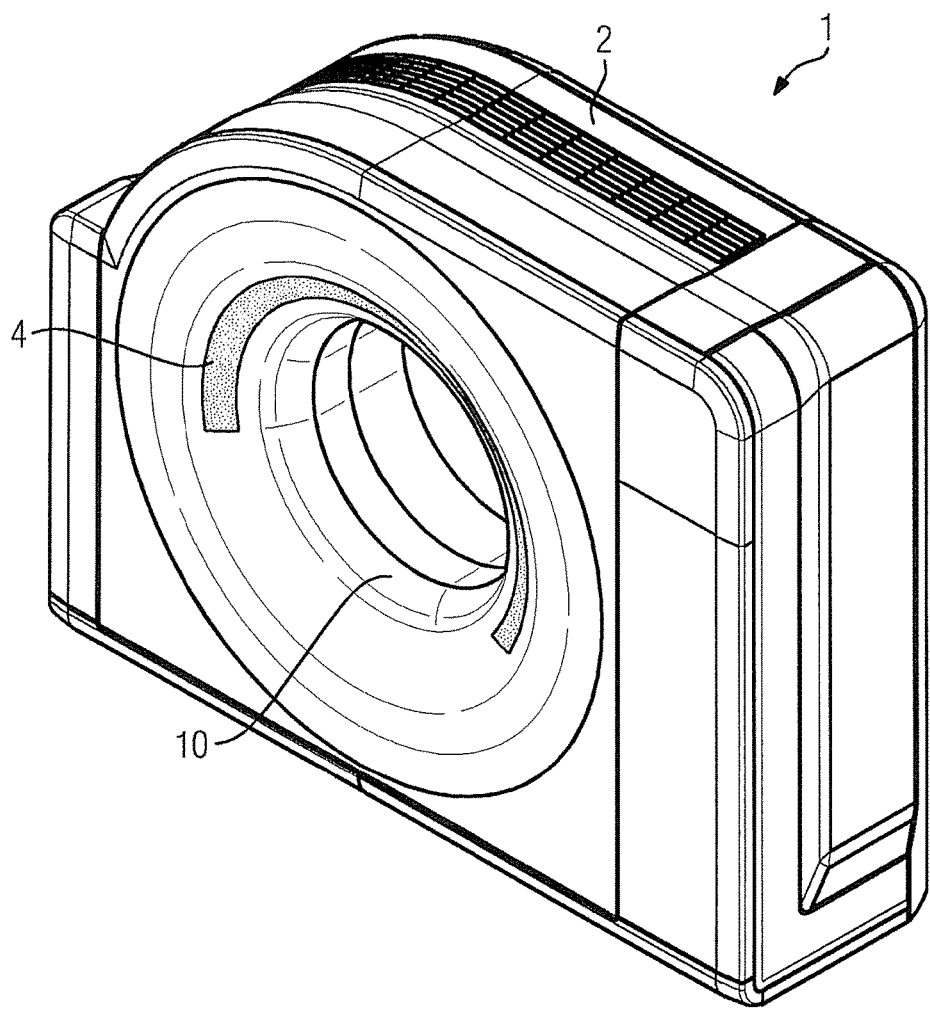
FIG. 2 shows a transverse view of an inventive tomography device in the form of a computed tomography system.

FIG. 2 shows a transverse view of an inventive tomography device in the form of a computed tomography system 1. The gantry of the computed tomography system 1 has a lining which forms a tunnel-shaped opening 5. Furthermore, in the embodiment of the inventive tomography device shown here, the lined gantry 2 has a funnel-shaped taper 10, which opens into the tunnel-shaped opening 5. Due to the illuminant 4 integrated into the funnel-shaped taper 10, the computed tomography system 1 is designed to illuminate an examination region protruding into the tunnel-shaped opening 5 of the gantry 2. In this case the illuminant 4 is integrated such that the surface of the funnel-shaped taper 10 has a smooth transition to the light exit window of the illuminant 4. The light exit window is designed to be curved, so that a patient 3 and if appropriate the examination region thereof protruding through the opening 5 can be illuminated from above. The surface of the gantry 2, and thus the funnel-shaped taper 10, as well as the tunnel-shaped opening 5, are essentially formed by the lining of the gantry 2. The surface of the gantry 2, in particular the part facing the patient 3, as well as the light exit window are designed to be smooth, so that the gantry can be easily and quickly cleaned. In particular when using the tomography device for invasive treatments it is necessary for it to be possible to clean the surface of the gantry easily and quickly.

Due to the inventive integrated illuminant 4 the conditions for treating the examination region are improved in the case of a simultaneous tomographic image recording, so that the person carrying out the treatment is guaranteed greater scope of movement with simultaneous illumination of the examination region. Since there is a smooth transition from the surface of the gantry 2 to the light exit window of the illuminant 4, the illuminant 4 does not protrude, thus reducing the risk of a collision between a person carrying out treatment and/or a medical instrument with the illuminant 4. Furthermore, it is easier to clean the surface of the gantry 2 and of the light exit window because of the non-protruding construction of the illuminant 4 and the avoidance of abutting edges.

The wide-area illuminant 4 can be a continuous illuminant 4, for example in the form of a panel of a plurality of light-emitting diodes (LED for short), or else discrete lighting elements 12 which can be controlled separately from one another and which have a common light exit window. The light exit window of the illuminant 4 can be formed either of plastic or of glass. Lighting elements 12 that can be controlled separately from one another are for example spotlights in the form of halogen lamps or separate LED panels. If the illuminant 4 is designed in the form of lighting elements 12 which can be controlled separately from one another, the lighting elements 12 can in another embodiment of the invention also each have a separate light exit window. Such light exit windows can have any shape, i.e. they can be designed as circles, ovals, rectangles, etc.

It is important that the light generated by the lighting element 4 can achieve sufficient brightness values as are customary for medical, in particular invasive, treatments. In respective embodiments of the invention the illuminant 4 is designed to generate a brightness of up to 5,000, 10,000, 20,000 or 50,000 lux. The illuminant 4 is further designed to emit light perceived to be white, since colored lighting does not permit a true-to-life perception of the illuminated region, as is necessary in the case of medical treatments.

Figure 3:
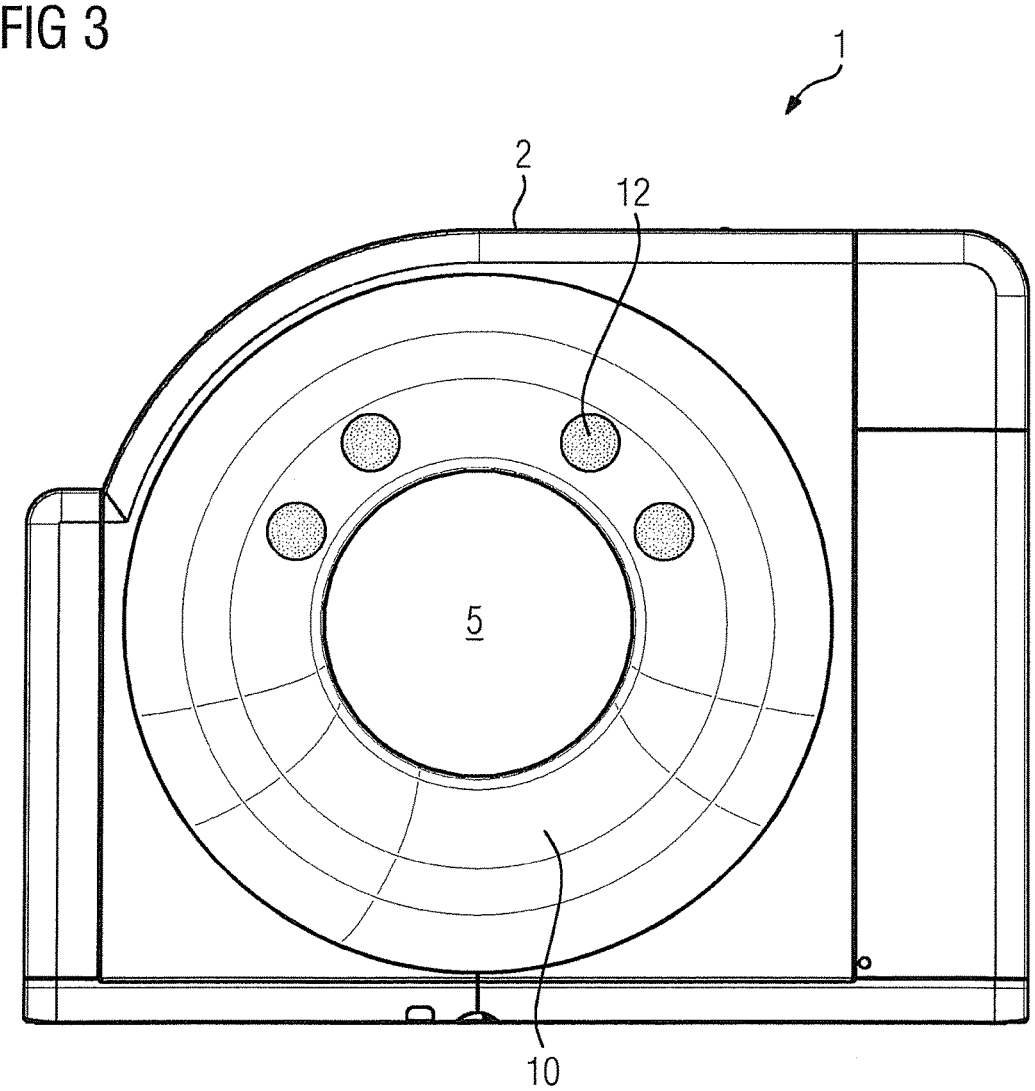
FIG. 3 shows a front view of an inventive tomography device in the form of a computed tomography system.

FIG. 3 shows a front view of an inventive tomography device in the form of a computed tomography system 1, wherein the illuminant 4 is designed in the form of a plurality of lighting elements 12 with round light exit windows. The lighting elements 12 are integrated into the funnel-shaped taper 10 of the gantry 2. The lighting elements 12 can be controlled separately from one another, so that their brightness as well as their orientation can also be controlled individually. In particular, the lighting elements 12 can be controlled such that their light is oriented onto a particular localized region. The control can for example take place via the orientation of individual mirrors integrated into the gantry, which selectively reflect the light emitted by the lighting elements 12. However, pivotable lighting elements 12 can also be used for control, which for example can be selectively pivoted using a small electric motor. Such control makes it possible to adjust the lighting to the respective treatment and/or patient geometry. Furthermore, additional lighting elements 12 can be integrated into the tunnel-shaped opening 5.

In the embodiment shown here the lighting element 4 extends radially along the funnel-shaped taper 10, thereby ensuring a particularly even illumination of the examination region and/or of another region to be illuminated. Due to the different angles of incidence of the light cones of the lighting elements 12 the shadow that is produced by the light cone of a particular lighting element 12 is illuminated by the light cone of another lighting element 12.

Figure 4:
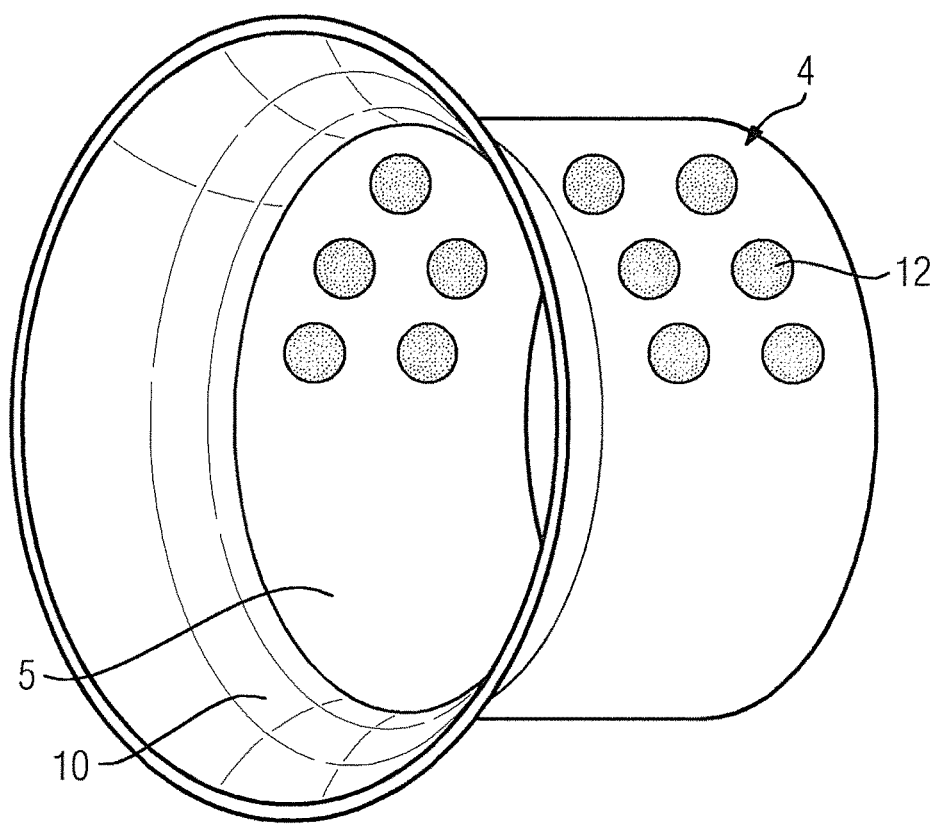
FIG. 4 shows the inner lining of the gantry with integrated lighting elements.

FIG. 4 shows the inner lining of the gantry 2 with integrated lighting elements 12. In the embodiment shown here the lighting elements 12 form the illuminant 4 which is integrated into the tunnel-shaped opening 5 of the gantry 2. As a result, as much direct illumination as possible of the examination region is allowed during a simultaneous tomographic recording of the examination region.

Furthermore, the illuminant 4 extends axially along the tunnel-shaped opening 5 of the gantry 2, so that the examination region is illuminated axially from different directions and hence the shadow cast is reduced. Furthermore, more lighting elements 12 than shown here can be integrated into the tunnel-shaped opening 5 of the gantry, in both the axial and the radial direction, thereby permitting a still more uniform illumination of the examination region.

Furthermore, all embodiments of the tomography device shown may be both a CT device, i.e. a computed tomography system 1, or else an MRT device.

Although modifications and changes may be suggested by those skilled in the art, it is the intention of the inventor to embody within the patent warranted heron all changes and modifications as reasonably and properly come within the scope of his contribution to the art.

I claim as my invention:

1. A tomography apparatus comprising:
   a gantry having a tunnel-shaped opening proceeding therethrough in an axial direction and defining an examination region adapted to receive a patient therein, said gantry having an exterior surface said tunnel-shaped opening having a constant diameter along said axial direction;
   a plurality of electronic components configured to rotate around said tunnel-shaped opening in order to acquire tomographic data from a portion of the patient situated in said examination region of said gantry;
   said gantry comprising a funnel-shaped taper leading to an entrance of said tunnel-shaped opening, said funnel-shaped taper having a smallest diameter, adjacent to said tunnel-shaped opening, and a largest diameter at an end of said funnel-shaped opening farthest from said tunnel-shaped opening; and
   an illuminant integrated into said funnel-shaped taper of said gantry, said illuminant comprising a light exit window through which light proceeds from said funnel-shaped taper so as to be oriented to illuminate at least a portion of said examination region in said tunnel-shaped opening, said light exit window forming a portion of said exterior surface of said gantry and having a smooth transition to a remainder of said exterior surface of said gantry.

2. A tomography apparatus as claimed in claim 1 wherein said illuminant comprises a plurality of individual lighting elements, and wherein said electronic components include a lighting control component configured to control the individual lighting elements separately from each other.

3. A tomography apparatus as claimed in claim 1 wherein said illuminant emits said light along a propagation direction, and wherein said illuminant is configured to allow said direction of propagation of said light to be selectively adjusted.

4. A tomography apparatus as claimed in claim 1 wherein said illuminant is configured to simultaneously illuminate at least said portion of said examination region from multiple directions, thereby reducing a shadow cast by said illuminant.

5. A tomography apparatus as claimed in claim 1 wherein said illuminant proceeds radially along said tunnel-shaped opening.

6. A tomography apparatus as claimed in claim 1 wherein said illuminant proceeds axially along said tunnel-shaped opening.

7. A tomography apparatus as claimed in claim 1 wherein said illuminant is configured to direct light emitted thereby onto a localized region of said examination region.

8. A tomography apparatus as claimed in claim 1 wherein said illuminant is comprised of at least one light-emitting diode.

9. A tomography apparatus as claimed in claim 1 wherein said illuminant is comprised of at least one halogen lamp.

10. A tomography apparatus as claimed in claim 1 wherein said plurality of components are configured to obtain computed tomography data from said portion of said patient in said examination region, as said tomographic data.

11. A tomography apparatus as claimed in claim 1 wherein said plurality of components are configured to obtain magnetic resonance tomography data from said portion of said patient in said examination region, as said tomographic data.

* * * * *